United States Patent [19]

Moszner et al.

[11] Patent Number: 6,057,460
[45] Date of Patent: May 2, 2000

[54] POLYMERIZABLE HYBRID MONOMERS

[75] Inventors: Norbert Moszner, Eschen; Volker Rheinberger; Frank Zeuner, both of Vaduz, all of Liechtenstein

[73] Assignee: Ivoclar AG, Liechtenstein

[21] Appl. No.: 08/804,204

[22] Filed: Feb. 21, 1997

[30] Foreign Application Priority Data

Feb. 22, 1996 [DE] Germany .................. 196 08 313

[51] Int. Cl.$^7$ ............... C07D 307/935; C07C 69/007; C07C 69/73; C07C 69/74
[52] U.S. Cl. .............. 549/463; 549/465; 560/120; 560/188; 560/194; 564/188
[58] Field of Search ............... 549/465, 463; 526/282; 560/120, 188, 194; 564/188

[56] References Cited

U.S. PATENT DOCUMENTS 3,681,438  8/1972  Starcher et al. .................. 526/282
4,808,638  2/1989  Steinkraus et al. .

OTHER PUBLICATIONS

"Grant & Haackh's Chemical Dictionary", 5th ed., Grant et al., McGraw–Hill Book co., New York, pp. 24, 53 (1987).

Moore et al., "Catalyzed Addition of Furan with Acrylic Monomers," *J. Org. Chem.*, 48:1105–1106 (1983).

Dauben et al., "Organic Reactions at High Pressure. Cycloadditions with Furans," *J. of the Amer. Chem. Soc.*, 98:1192–1193 (1976).

Lipshutz, Bruce, "Five–Membered Heteroaromatic Rings as Intermediates in Organic Synthesis," Chemical Reviews, 795–819 (1986).

Tian et al., "Novel Preparation of 1– and 3–Substituted Bicyclo[3.2.2]nona–3,6,8–trien–2–ones from Tropones 2,3–Bis(methoxycarbonyl)–7–oxabicyclo–[2.2.1] heptadiene by High–Pressure Cycloaddition–Thermal Cycloreversion Procedure," *Bull Chem. Soc. Jap.*, 61:2393–2399 (1988).

Klunder et al., "Crystal and Molecular Structure of (2R, 3R)–2–exo–((1R)–1–hydroxy–2–methyl–propyl)–3–exo Hydroxymethyl–bicyclo[2.2.1]–hept–5–ene, $C_{12}H_{20}O_2$," *J. Chem. Cryst.*, 25(7):389–392 (1995).

North et al., "Asymmetric Desymmetrisation of Meso–Norbornene Anhydrides Utilising Methyl Prolinate As a Chiral Regent," *Synlett*, 639–640 (1995).

*Primary Examiner*—Donald R. Wilson
*Attorney, Agent, or Firm*—Nixon Peabody LLP

[57] ABSTRACT

Polymerizable hybrid monomers with norbornenyl or norbornadienyl groups are described which can be radically cured at room temperature and are suitable in particular for use in the dental field.

7 Claims, No Drawings

POLYMERIZABLE HYBRID MONOMERS

The invention relates to polymerizable hybrid monomers, a process for the preparation thereof, the use thereof in particular as dental material, a dental material containing them, and to polymers or copolymers obtainable therefrom.

Compounds with at least two groups polymerizing according to the same mechanism, such as divinyl compounds, di-, tri- or tetra(meth)acrylates, bismaleinimides or diepoxides, are widely used as cross-linking monomers, inter alia in the preparation of adhesives, laquers and composites (cf S. C. Ling, E. M. Pearce, "High-Performance Thermosets, Chemistry, Properties, Applications" in S. P. Pappas (Editor), Radiation Curing—Science and Technology, Plenum Press, New York-London 1992). In contrast, monomers with at least two groups polymerizing according to different mechanisms, so-called ambifunctional monomers or hybrid monomers, are of interest for the selective synthesis of crosslinkable polymers.

Depending on the nature of the polymerizable groups, the one-stage or two-stage synthesis of polymer networks by using hybrid monomers may be achieved by a combination of, for example, radical and cationic vinyl polymerization, e.g. in the case of vinyloxyethyl methacrylate, of radical vinyl polymerization and cationic ring-opening polymerization, e.g. in the case of glycidyl methacrylate, of anionic group transfer polymerization and radical polymerization, e.g. in the case of acryloyloxyethyl methacrylate, or of ring-opening metathesis polymerization and radical ring-opening polymerization, e.g. in the case of cyclooct-5-enyl methacrylate.

In this connection, bicyclic compounds with bicyclo[2.2.1]hept-2-enyl (norbornenyl) or 7-oxa-bicyclo[2.2.1]hept-2-enyl groups and those with bicyclo[2.2.1]hept-2,5-dienyl groups (norbornadienyl) are also of interest, since they are suitable as monomers for ring-opening metathesis polymerization (D. J. Brunelle (Ed.), Ring-Opening Polymerization, Hanser Pub. Munich etc. 1993, page 129). Moreover, according to U.S. Pat. No. 4,808,638 norbornene compounds can also be used as reactive ene-components for low-shrinkage thiol-ene polymerization.

Hybrid monomers having three groups polymerizable according to different mechanisms have not however become known hitherto.

The object of the invention is to provide polymerizable hybrid monomers which can be cured at room temperature, can be polymerized by means of radical polymerization in combination with either ionic polymerization or ring-opening metathesis polymerization and can be used as a constituent of dental materials, in particular as an adhesion-enhancing component of dentine adhesives.

This object is achieved by the polymerizable hybrid monomers according to the present invention.

The subject-matter of the present invention is also the process for the preparation of the polymerizable hybrid monomers according to claims 5 and 6, their use according to claims 5 and 6, dental materials containing them, and polymers or copolymers which may be obtained by polymerization or copolymerization of the hybrid monomers.

The polymerizable hybrid monomers according to the invention are compounds of the following formula (I), and also stereoisomeric compounds and any mixtures of all of these

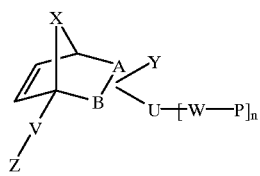
(I)

where A-B, X, Z, V, Y, R, U, $R^1$, W, P and n independently of one another have the following meanings:

A-B=C—C or C=C;

X=$CH_2$ or O;

Z=$CH_2$=CH—CO— or $CH_2$=C($CH_3$)—CO—;

V=$CH_2$—O or $CH_2$—NH;

Y=H, substituted or unsubstituted $C_1$ to $C_{12}$ alkyl, substituted or unsubstituted $C_6$ to $C_{14}$ aryl, halogen, $NO_2$, $NH_2$, $NR_2$, OH, OR, CN, CHO, CO—R, COOH, CO—$NH_2$, CO—OR, $CH_2$=CH—, $CH_2$=CH—CO—, $CH_2$=C($CH_3$)—CO—, SH or S—R, where R=substituted or unsubstituted $C_1$ to $C_{12}$ alkyl or substituted or unsubstituted $C_6$ to $C_{14}$ aryl;

U=CO—$R^1$, CO—$NHR^1$, CO—$OR^1$, O—CO—$NHR^1$, NH—CO—$OR^1$, O—$R^1$, S—$R^1$ or is absent, where $R^1$=$C_1$ to $C_5$ alkylene or oxyalkylene or $C_6$ to $C_{12}$ arylene;

W=O, NH, CO—O, CO—NH, O—CO—NH or is absent;

p=a polymerizable group, in particular a (meth)acrylic, vinyl, allyl, allyl ether, vinyl ether, epoxy or styryl group; and n=1 to 4.

Suitable examples of P are as follows:

p=$CH_2$=CH—, $CH_2$=CH—CO—, $CH_2$=C($CH_3$)—CO—, $CH_2$=CH—$CH_2$—, $CH_2$=CH—O—$CH_2$—$CH_2$—, $CH_2$=CH—O—, $CH_2$=CH—$CH_2$—O—,

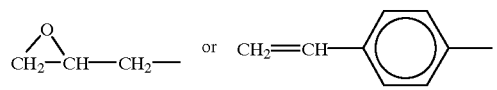

The above formula (I) covers only those compounds which are compatible with the valency theory. Furthermore, formula (I) stands for the two position isomers

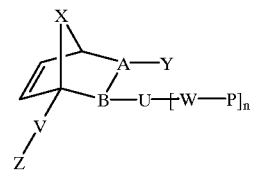

and

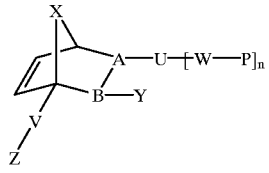

This also applies accordingly to the further formulae given in the description and in the claims, in which the form of representation used in formula (I) is used to embrace both position isomers. Moreover, the Y and U groups are bound independently of one another in the endo or exo position.

The structure element [W-P]$_n$ means that U is substituted n times by W-P. If U=is absent, either the carbon atom A or B is substituted n times by W-P.

The substituents optionally present in the case of the Y and R radicals are in particular COOH, OH, halogen, C$_1$ to C$_{12}$ alkoxy, —N$^+$—(C$_1$ to C$_{12}$-alkyl)$_3$, —O—P=O(OH)$_2$ or —P=O(OH)$_2$. It is possible that Y and R are substituted several times.

Typically, the hybrid monomers according to the invention are present in the form of stereoisomer mixtures, in particular as racemates.

Preferred definitions, which may be chosen independently of one another, exist for the above-mentioned variables of formula (I), and these definitions are as follows:

A-B=C—C or C=C,
X=O,
Z=CH$_2$=C (CH$_3$)—CO—,
V=CH$_2$—O,
Y=COOH, CN or CO—NH$_2$,
R=substituted or unsubstituted C$_1$ to C$_4$ alkyl,
U=CO—OR$^1$ or CO—NHR$^1$,
R$^1$=C$_1$ to C$_3$ alkylene,
W=O, NH, CO—O or is absent,
P=a vinyl ether, epoxy, allyl, styryl or (meth)acrylic group; and/or
n=1 or 2.

Preferred compounds are, therefore, those in which at least one of the variables of the formula (I) has the preferred definition described above.

Particularly preferred monomers according to the invention are those which contain at least three groups polymerizable according to different mechanisms.

The hybrid monomers (I) according to the invention are produced by initially preparing, as an intermediate, by way of a Diels-Alder reaction of the substituted diene(meth)acrylic compound (II) with the substituted dienophile (III), a correspondingly substituted norbornene or norbornadiene compound (IV), which, by way of a normal nucleophilic substitution (cf Various authors, Organikum, Deutscher Verlag der Wissenschaften, Berlin, 1973), is then reacted with the polymerization group-containing educt P-W-H.

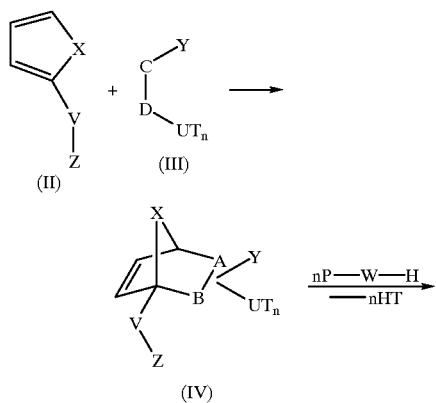

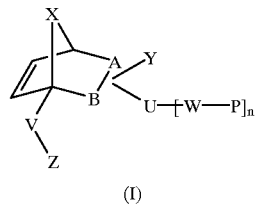

Here,
C—D=C=C or C≡C;
H=hydrogen; and
T=halogen, OH or OR
and the remaining variables are as defined above.

The substituted diene(meth)acrylic compound used (II) can generally be obtained by reacting suitably substituted furans (X=O) or cyclopentadienes (X=CH$_2$) with a corresponding (meth)acrylic compound according to the reaction equation below

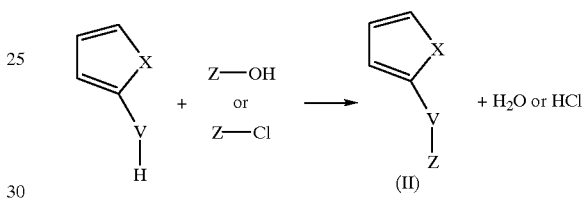

Particularly suitable as dienophiles (Y-C-D-UT$_n$) are derivatives of maleic acid or acetylene dicarboxylic acid, e.g. maleic acid- 2-hydroxyethyl monoester or acetylene dicarboxylic acid-2-hydroxyethyl monoester.

Thus furfuryl (meth)acrylate, which can be obtained simply by esterification of furfuryl alcohol with (meth)acrylic acid chloride or anhydride or by transesterification of furfuryl alcohol with methyl (meth)acrylate, can be used e.g. for the preparation of hybrid monomers according to the invention in which X=O. The furfuryl (meth)acrylate is then reacted e.g. with maleic acid anhydride by a Diels-Alder reaction (cf H. Wollweber, Diels-Alder-Reaktion, G. Thieme-Verlag 1972) to form the bicyclic anhydride (A) which has the chemical name exo-1-(methacryloyloxymethyl)-7-oxa-bicyclo[2.2.1]hept-5-ene-2,3-dicarboxylic acid anhydride. Finally, the corresponding hybrid monomer is obtained in a simple manner by further reaction of (A) with a polymerizable alcohol, such as 4-hydroxystyrene, ethylene glycol monovinyl ether, allyl alcohol or 2-hydroxyethyl (meth)acrylate. This reaction sequence is explained below using as an example the reaction of the bicyclic anhydride (A) with 4-hydroxystyrene:

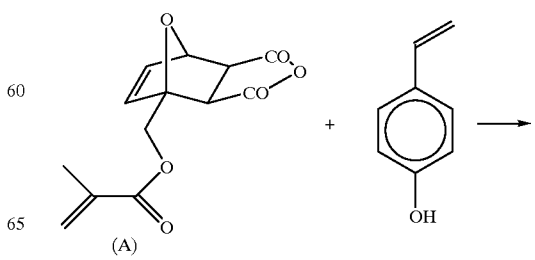

-continued

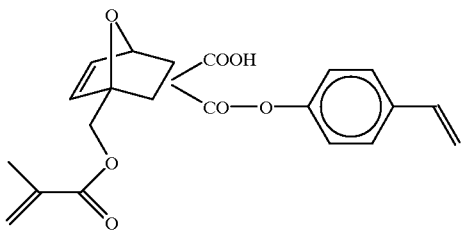

The polymerizable groups of the hybrid monomers according to the invention can be polymerized according to different mechanisms with the result that a multi-stage polymerization, the combination of various polymerization mechanisms or the synthesis of polymerizable polymers is possible.

Thus 7-oxa-bicyclo[2.2.1]heptenyl groups of the monomers according to the invention can be converted into polymers by a ring-opening metathesis polymerization under the conditions known from the literature (cf e.g. S.-Y. Lu et al. in Macromol. Chem. Phys. 195 (1994) 1273) e.g. in the presence of commercial ruthenium (III) chloride in aqueous-alcoholic medium. The (meth)acrylate groups can be polymerized according to known methods of radical polymerization (cf P. Rempp, E. W. Merill in Polymer Synthesis, Hüthig & Wepf Verlag, Basel 1986, page 91 et seq. and 114 et seq.), in which an acrylate group can be selectively polymerized in the presence of a methacrylate group with $ZnBr_2$ as catalyst by the group transfer polymerization (GTP) technique (cf D. Y. Sogah, W. R. Hertler, O. W. Webster, G. M. Cohen in Macromolecules 20 (1987) 1473).

Further polymerizable groups can then be polymerized according to another mechanism, as explained below with reference to some preferred hybrid monomers according to the invention.

In the case of the hybrid monomer (1) according to the invention, A-B=C—C, X=O, $V=CH_2O$, U=—$COO(CH_2)_2$—, W=is absent, n=1, Z=methacrylic radical, Y=COOH and P=styryl radical. This hybrid monomer contains three differently polymerizable groups, namely (1st) the 7-oxa-bicyclo[2.2.1.]hept-2-enyl group which can undergo a ring-opening metathesis polymerization, (2nd) the styryl group which can be cationically homo- or copolymerized and (3rd) the methacrylate group which can be radically polymerized or copolymerized.

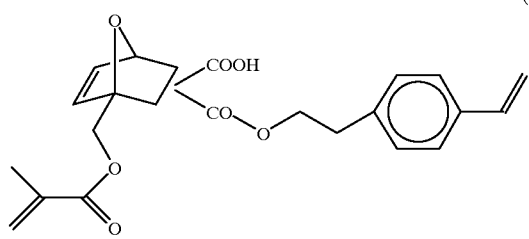

A further example is the hybrid monomer (2) according to the invention in which A-B=C—C, X=O, $V=CH_2O$, U=—$COO(CH_2)_2$—, W=is absent, n=1, Z=methacrylic radical, Y=COOH and P=vinyl ether radical. This hybrid monomer likewise contains three differently polymerizable groups and can initially be converted by a ring-opening metathesis polymerization of the 7-oxa-bicyclo[2.2.1.]hept-2-enyl group into a polymer which then can be cross-linked in two further steps, e.g. initially radically via the methacrylic group and then cationically via the vinyl ether group.

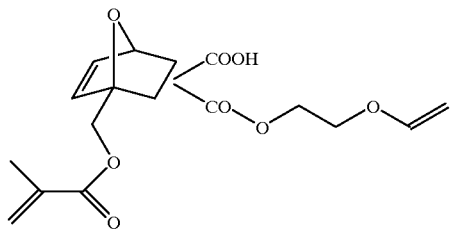

A further example is finally the hybrid monomer (3) according to the invention in which A-B=C—C, X=O, $V=CH_2O$, U=—$COO(CH_2)_2$—, O, W=is absent, n=1, Z=methacrylic radical, Y=COOH, P=acrylic group. The acrylate group of this hybrid monomer can initially be selectively polymerized following protection of the carboxyl group, e.g. using a trimethylsilyl radical, by using the technique of group transfer polymerization (GTP). The resulting polymer-bound methacrylate groups can then be copolymerized in a second step, e.g. in solution with other methacrylates, i.e. be used to form corresponding graft branches. The graft copolymer obtained can finally also be cross-linked via the norbornenyl groups present.

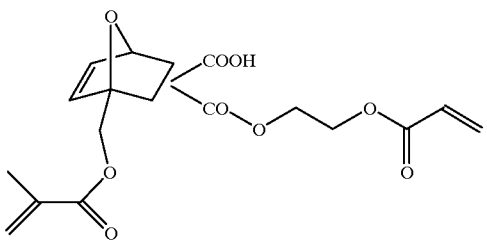

The structural formulae of further preferred hybrid monomers (4) to (6) are listed below.

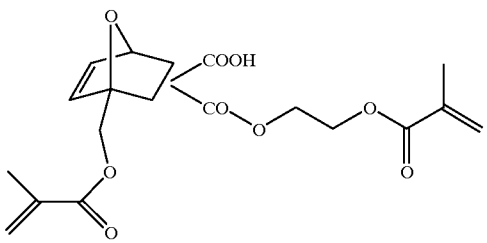

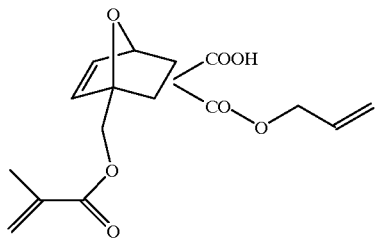

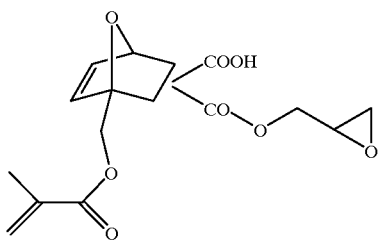

(6)

Due to the presence of polymerizable groups, the hybrid monomers according to the invention are suitable as starting materials for the preparation of polymers and copolymers. Depending on the nature of the polymerizable groups and taking into account possible side reactions through existing further functional groups, they can be homopolymerized in stages by means of known methods of radical or ionic polymerization or of ring-opening metathesis polymerization or be copolymerized together with suitable comonomers.

Moreover, the hybrid monomers according to the invention and polymers and copolymers obtained therefrom can be functionalized via remaining polymerizable groups, such as e.g. by addition of SH or NH groups of suitably functionalized compounds to the remaining polymerizable groups. Thus e.g. the hybrid monomer (2) can initially be radically polymerized using only the methacrylate groups. Then e.g. the commercial 3-mercaptopropyl trimethoxysilane can be added to the remaining double bonds.

The hybrid monomers according to the invention can accordingly be used both for the preparation of stepwise polymerizable homopolymers and as comonomers, with further reactions, such as cross-linking or coupling reactions or copolymerisations, of the copolymers formed being possible due to existing further polymerizable groups. Moreover, the hybrid monomers according to the invention allow the combination of monomer units of anionically or radically polymerizable (meth)acrylates with the cationically polymerizable vinyl ethers. Finally, additional functional groups of the monomers according to the invention, such as acid carboxylic or phosphonic acid groups, can be advantageous when using the monomers in adhesives since they can contribute to the increasing of the adhesion of the adhesives to various substrates, such as plastic or metal.

If desired, the hybrid monomers according to the invention or polymers obtained therefrom can be modified by addition of additives, such as fillers, pigments, plasticizers and stabilizers.

The hybrid monomers according to the invention can be used as a constituent of unfilled monomer mixtures curable by polymerization, e.g. for adhesives, or of filled compositions curable by polymerization, e.g. for the preparation of composite materials. In this connection it proves to be an advantage that the hybrid monomers allow a combination of monomers polymerizing according to different mechanisms.

The hybrid monomers according to the invention are preferably used as dental material or a constituent of dental material, in particular as a constituent of dentine adhesives. In addition to an adhesion-improving effect their ability to be cured radically at room temperature proves to be advantageous for this application.

The hybrid monomers according to the invention are particularly preferably used as a constituent of dental materials in a quantity of 0.1 to 60, in particular 5.0 to 45, wt. %.

When the hybrid monomers according to the invention are used as a constituent of dental materials, they are advantageously combined with polymerizable organic binders, fillers, initiators and/or further additives, such as conventional stabilizers, e.g. hydroquinone monomethyl ether (MEHQ) or 2,6-di-tert.-butyl-4-methylphenol (BHT), UV absorbers, pigments, dyes or solvents.

Suitable as polymerizable organic binders are all binders which can be used for a dental material, in particular monofunctional or polyfunctional (meth)acrylates which can be used alone or in mixtures. Preferred examples of these compounds are methyl (meth)acrylate, isobutyl (meth) acrylate, cyclohexyl (meth)acrylate, tetraethylene glycol di(meth)acrylate, triethylene glycol di(meth)acrylate, diethylene glycol di(meth)acrylate, ethylene glycol di(meth) acrylate, polyethylene glycol di(meth)acrylate, butanediol di(meth)acrylate, hexanediol di(meth)acrylate, decanediol di(meth)acrylate, dodecanediol di(meth)acrylate, bisphenol-A-di(meth)acrylate, trimethylolpropanetri(meth)acrylate, 2,2-bis-4-(3-methacryloxy-2-hydroxypropoxy)-phenylpropane (bis-GMA) and the products of the reaction of isocyanates, in particular di- and/or triisocyanates, with OH group-containing (meth)acrylates. Particularly preferred examples of the last-mentioned products are obtainable by reaction of 1 mol of hexamethylene diisocyanate with 2 mol of 2-hydroxyethylene methacrylate, of 1 mol of tri-(6-isocyanatohexyl)biuret with 3 mol of 2-hydroxyethyl methacrylate and of 1 mol of 2,2,4-trimethylhexamethylene diisocyanate with 2 mol of 2-hydroxyethyl methacrylate.

These organic binders are normally used in the dental material according to the invention in a quantity of 0.1 to 60 wt. %.

Examples of preferred fillers are quartz powder, glass ceramic powder and glass powder, in particular barium silicate glass, Li/Al silicate glass and barium glass powder, aluminium oxides or silicon oxides, very finely divided silicas, in particular pyrogenic or precipitated silicas, X-ray-opaque fillers such as ytterbium trifluoride.

The fillers are typically used in a quantity of 0 to 80 wt. %.

The dental materials according to the invention can be polymerized by heat, in the cold or by light. The known peroxides such as dibenzoyl peroxide, dilauroyl peroxide, tert.-butylperoctoate or tert.-butylperbenzoate can be used as initiators for hot polymerization. Moreover, 2,2'-azoisobutyric acid nitrile (AIBN), benzpinacol and 2,2'-dialkylbenzpinacols are also suitable.

For example, benzophenone and derivatives thereof as well as benzoin and derivatives thereof can be used as initiators for photopolymerization. Further preferred photoinitiators are the α-diketones such as 9,10-phenanthrenequinone, diacetyl, furil, anisil, 4,4'-dichlorobenzil and 4,4'-dialkoxybenzil. Camphor quinone is particularly preferably used. Moreover, the group of acyl phosphine oxides is also highly suitable for the initiation of photopolymerization. In order to accelerate the initiation, the photoinitiators are used preferably together with a reducing agent, particularly preferably with an amine, in particular an aromatic amine.

Radical-supplying redox systems, for example benzoyl or lauroyl peroxide together with amines such as N,N-dimethyl-p-toluidine, N,N-dihydroxyethyl-p-toluidine or other structurally related amines are used as initiators for cold polymerization.

The combination of photoinitiators with different redox systems has proved advantageous especially in the case of dental materials for the cementing of dental restorations, such as glass ceramic inlays, onlays, partial crowns and crowns. Combinations of camphor quinone, benzoyl peroxide and amines, such as N,N-dimethyl-p-toluidine and/or N,N-cyanoethylmethylaniline, are preferred.

The concentration of initiators preferably lies in the range from 0.05 to 1.5 wt. %, particularly preferably in the range from 0.2 to 0.8 wt. %, relative to the quantity of monomers used.

The invention is explained in more details below with reference to examples.

EXAMPLES

Example 1

Synthesis of the bicyclic anhydride (A) (exo-1-(methacryloyloxymethyl)-7-oxabicyclo[2.2.1]hept-5-ene-2,3-dicarboxylic acid anhydride 1 mol (166 g) of furfuryl methacrylate and 1.1 mol (107.8 g) of maleic acid anhydride were suspended in a 500 ml three-necked flask having a mechanical stirrer, thermometer and calcium chloride drying tube, together with 10 mg of hydroquinone monomethyl ether (MEHQ) in 250 ml of butyl acetate which has been dried using a molecular sieve and were stirred for 2 days at room temperature. The initially cloudy dispersion became clear after ca 1 hour, and after approximately one day the product formed as a solid precipitate (ca 130 g), which was filtered off, washed with butyl acetate and dried in vacuo until a constant weight was obtained. Further product was isolated from the filtrate after a few days, so that in total 188 g (70% yield) of an almost colourless crystalline substance were obtained.

Elemental analysis ($C_{13}H_{12}O_6$: Calc.: C, 59.08; H, 4.58. Found: C, 58.89; H, 4.61.

$^1$H-NMR (CDCl$_3$, ppm: 1.91 (s, 3H, CH$_3$), 3.42 and 3.52 (d, 2H, CH— 2,3-exo), 4.55 and 4.83 (d, 2H, CH$_2$O), 5.33 (s, 1H, —CH<), 5.67 and 6.04 (s, 2H, CH$_2$=), 6.52 (d, 2H, —CH=).

IR (KBr, cm$^{-1}$): 1630 (C=C), 1720 (C=O-ester), 1780 and 1860 (C=O-anhydride).

Example 2

Synthesis of the exo-1-[(methacryloyloxy)methyl]-7-oxabicyclor[2.2.1]hept-5-ene-2,3-dicarboxylic acid monoallyl ester (5)

41 mmol (2.32 g) of allyl alcohol and 10 mg of phenothiazine were dissolved with stirring in 50 ml of anhydrous tetrahydrofuran (THF) in a 100 ml two-necked flask, and 40 mmol (10.6 g) of bicyclic anhydride (A), which had been prepared according to Example 1, were then suspended in this solution. After cooling to 10° C., a solution of 40 mmol (4.0 g) of triethylamine (TEA) and 0.25 g of 4-dimethylaminopyridine (DMAP) in 10 ml of THF was added dropwise over a period of 20 minutes. After heating to room temperature, stirring was continued for a further 2 hours to complete the reaction. The reaction mixture was taken up in a mixture of 100 ml of 10% aqueous NaHCO$_3$ solution and 50 ml of methylene chloride. The aqueous phase was separated off and shaken out with methylene chloride, adjusted to pH=1–2 with concentrated hydrochloric acid and extracted again with methylene chloride. The combined methylene chloride phases were then dried over anhydrous Na$_2$SO$_4$ and freed of the solvent in vacuo at a temperature of below 25° C. The resultant solid residue was dissolved in methylene chloride and precipitated out with the addition of petroleum ether. After filtering off and drying, 4.3 g (33% yield) of white crystals were obtained.

Elemental analysis ($C_{16}H_{18}O_7$): Calc.: C, 59.63; H, 5.63. Found: C, 59.50; H, 5.59.

$^1$H-NMR (CDCl$_3$, ppm: 1.95 (s, 3H, CH$_3$); 3.05 (m, 2H, H-2,3); 4.6 (d, 2H, COOCH$_2$); 4.75 (d, 2H, CH$_2$, CH$_2$—O-methacrylate); 5.2 (m), 5.35 (d) and 6.0 (m, 3H, CH=CH$_2$-allyl); 5.35 (d, 1H, H-4); 5.6 and 6.2 (s, 2H, CH$_2$=methacrylate); 6.45 (m, 2H, H-5,6); 8.85 (s, 1H, COOH).

IR (KBr, cm$^{-1}$): 709 (m), 815 (w), 870 (m), 934 (s), 989 (m), 1108 (w), 1177 (s), 1297 (s), 1422 (m), 1638 (m), 1718 (s), 2957 (m).

Example 3

Synthesis of the exo-1-[(methacryloyloxy)methyl]-7-oxabicyclo[2.2.1]hept-5-ene-2,3-dicarboxylic acid mono [(2-methacryloyloxy)ethyl]ester (4)

41 mmol (5.33 g) of 2-hydroxyethyl methacrylate (HEMA) and 0.01 g of MEHQ were dissolved in 50 ml of THF in a 100 ml two-necked flask with magnetic stirrer and drying tube, and 40 mmol (10.6 g) of bicyclic anhydride (A) were added to this solution. A solution of 40 mmol (4.0 g) of triethylamine and 0.25 g of DMAP in 10 ml of THF was slowly added dropwise accompanied by stirring and cooling with ice (T<10° C.). After addition was complete, the white suspension became clear and cream-coloured. The reaction was terminated after 30 minutes by adding the reaction mixture to 50 ml of methylene chloride and treating the mixture obtained with 120 ml of 10% aqueous NaHCO$_3$ solution. The organic phase was separated off. The aqueous phase was extracted once more with 50 ml of methylene chloride and adjusted to a pH≈2 with concentrated hydrochloric acid accompanied by cooling. A thick white liquid was precipitated and was taken up in 300 ml of methylene chloride. The aqueous phase was separated off and extracted three times with in each case 150 ml of methylene chloride. Then the combined organic phases were stabilized with some 2,6-di-tert.-butyl-4-methylphenol (BHT) and dried over Na$_2$SO$_4$. After the distilling off of the solvent in vacuo at a temperature of below 25° C., a yellow oil was obtained. After drying under medium high vacuum, the result was a yield of 6.6 g (42%) of (4), the product containing ca 7% HEMA.

Elemental analysis ($C_{19}H_{22}O_9$): Calc.: C, 57.87; H, 5.62. Found: C, 56.32; H, 5.72.

$^1$H-NMR (CDCl$_3$, ppm): 1.95 (s, 3H, CH$_3$); 3.0 (m, 2H, H-2,3); 4.4 (s, 2×2H, COOCH$_2$); 4.75 (m, 2H, CH$_2$—O-methacrylic); 5.4 (s, 1H, H-4); 5,6 and 6.2 (s, 2×2H, CH$_2$=methacrylic); 6.45 (m, 2H, H-5,6); 8.8 (s, 1H, COOH).

IR (KBr, cm$^{-1}$): 733 (w), 815 (w), 939 (m), 1164 (s), 1298 (m), 1453 (w), 1636 (m), 1721 (s), 2960 (m).

Example 4

Synthesis of the exo-1-[(methacryloyloxy)methyl]-7-oxabicyclo[2.2.1]hept-5-ene-2,3-dicarboxylic acid mono[(2-acryloyloxy)ethyl]ester (3)

41 mmol (4.93 g) of 2-hydroxyethyl acrylate (HEA) and 0.01 g of MEHQ were dissolved in 50 ml of THF in a 100 ml two-necked flask with magnetic stirrer and drying tube, and 40 mmol (10.6 g) of bicyclic anhydride (A) were added to this solution. A solution of 40 mmol (4.0 g) of TEA and 0.25 g of DMAP in 10 ml of THF was slowly added dropwise accompanied by stirring and cooling with ice (T<10° C.). After the addition was complete, the white suspension became clear and cream-coloured. The reaction was terminated after 30 minutes by adding the reaction mixture to 50 ml of methylene chloride and treating the mixture obtained with 120 ml of 10% aqueous $NaHCO_3$ solution. The organic phase was separated off. The aqueous phase was extracted once more with 50 ml of methylene chloride and adjusted to a pH of≈2 with concentrated hydrochloric acid accompanied by cooling. A thick white liquid was precipitated and was taken up in 300 ml of methylene chloride. The aqueous phase was separated off and extracted three times with in each case 150 ml of methylene chloride. The combined organic phases were then stabilized with BHT and dried over $Na_2SO_4$. After the distilling off of the solvent in vacuo at a temperature of below 25° C. and drying under medium high vacuum, (3) was obtained as a yellow oil in 65% yield (9.9 g), the product still containing ca 5% HEA.

Elemental analysis ($C_{18}H_{20}O_9$): Calc.: C, 56.85; H, 5.30. Found: C, 54.60; H, 5.35.

$^1$H-NMR ($CDCl^3$, ppm): 1.95 (s, 3H, $CH_3$); 3.1 (m, 2H, H-2,3); 4.4 (s, 2×2H, $COOCH_2$); 4.75 (d, 2H, $CH_2$—O-methacrylic); 5.4 (s, 1H, H-4); 5.6 to 6.2 (m, 5H, $CH_2$=methacrylic, $CH_2$=CH-acrylic); 6.45 (m, 2H, H-5, 6); 10.25 (s, 1H, COOH).

IR (KBr, $cm^{-1}$): 733 (w), 812 (m), 934 (m), 987 (m), 1075 (w), 1168 (s), 1298 (m), 1410 (m), 1636 (m), 1730 (s), 2960 (w).

Example 5

Synthesis of the exo-1-[(methacryloyloxy)methyl]-7-oxabicyclo[2.2.1]hept-5-ene-2,3-dicarboxylic acid mono[(2-vinyloxy)ethyl]ester (2)

41 mmol (3.5 g) of 2-hydroxyethylvinyl ether and 0.01 g of MEHQ were dissolved in 50 ml of THF in a 100 ml two-necked flask with magnetic stirrer and drying tube, and 40 mmol (10.6 g) of bicyclic anhydride (A) were added to this solution. A solution of 40 mmol (4.0 g) of triethylamine and 0.25 g of DMAP in 10 ml of THF was slowly added dropwise accompanied by stirring and cooling with ice (T<10° C.). After the addition was complete, the suspension obtained became clear and cream-coloured. The reaction was terminated after 30 minutes by adding the reaction mixture to 50 ml of methylene chloride and treating the mixture obtained with 120 ml of 10% aqueous $NaHCO_3$ solution. The organic phase was separated off. The aqueous phase was extracted once more with 50 ml of methylene chloride and adjusted to a pH of≈2 with concentrated hydrochloric acid accompanied by cooling. A thick white liquid was precipitated and was taken up in 300 ml of methylene chloride. The aqueous phase was extracted three times with in each case 150 ml of methylene chloride. The combined organic phases were then stabilized with BHT and dried over $Na_2SO_4$. After the distilling off of the solvent at a temperature of below 25° C. and drying under medium high vacuum, (2) was obtained as a yellowish oil in a 38.5% yield (5.4 g).

$^1$H-NMR ($CDCl_3$, ppm) 1.95 (s, 3H, $CH_3$); 3.0 (m, 2H, H-2,3); 3.7 (2H, $CH_2$—O); 4.25 (m, 2×2H, $COOCH_2$ and $CH_2$=); 4.75 (d, 2H, $CH_2$—O-methacrylic); 5.4 (d, 1H, H-4); 5.6 and 6.2 (s, 2H, $CH_2$=methacrylic); 6.5 (m, 2H, H-5,6 and 1H, O—CH=); 8.6 (s, 1H, COOH).

IR (KBr, $cm^{-1}$): 715 (w), 814 (w), 934 (w), 1077 (w), 1164 (s), 1299 (m), 1635 (w), 1723 (s), 2959 (w).

Example 6

Synthesis of the exo-1-[(methacryloyloxy)methyl]-7-oxabicyclo[2.2.1]hept-5-ene-2,3-dicarboxylic acid mono[(1,3-dimethacryloyloxy)propyl]ester (7)

41 mmol (9.12 g) of glycerin dimethacrylate and 0.01 g of MEHQ were dissolved in 50 ml of THF in a 100 ml two-necked flask with magnetic stirrer and drying tube, and 40 mmol (10.6 g) of bicyclic anhydride (A) were added to this solution. A solution of 40 mmol (4.0 g) of TEA and 0.25 g of DMAP in 10 ml of THF was slowly added dropwise accompanied by stirring and cooling with ice (T<10° C.). After the addition was complete, the white suspension became clear and cream-coloured. The reaction was terminated after 30 minutes by adding the reaction mixture to 50 ml of methylene chloride and treating the mixture obtained with 120 ml of 10% aqueous $NaHCO_3$ solution. The organic phase was separated off. The aqueous phase was extracted once more with 50 ml of methylene chloride and adjusted to a pH of≈2 with concentrated hydrochloric acid accompanied by cooling. A thick white liquid was precipitated and was taken up in 300 ml of methylene chloride. The aqueous phase was separated off and extracted three times with in each case 150 ml of methylene chloride. The combined organic phases were then stabilized with BHT and dried over $Na_2SO_4$. After the distilling off of the solvent in vacuo at a temperature of below 25° C. and drying under a medium high vacuum, (7) was obtained as a viscous oil in 17.8% yield (3.5 g).

$^1$H-NMR ($CDCl_3$, ppm) 1.95 (s, 3H, $CH_3$); 3.05 (m, 2H, H-2,3); 4.35 (m, 5H, $CH_2CH$—$CH_2$); 4.75 (d, 2H, $CH_2$—O-methacrylic); 5.45 (d, 1H, H-4); 5.6 and 6.2 (s, 2H, $CH_2$=methacrylic); 6.45 (m, 2H, H-5,6); 8.75 (s, H, COOH).

IR (KBr, $cm^{-1}$): 652 (w), 737 (w), 814 (m), 863 (w), 942 (m), 1017 (m), 1160 (s), 1296 (s), 1454 (m), 1638 (m), 1723 (s), 2960 (m).

Example 7

Synthesis of the exo-1-[(methacryloyloxy)methyl]-7-oxabicyclo[2.2.1]hept-5-ene-2,3-dicarboxylic acid mono(n-propyl)ester (8)

41 mmol (2.4 g) of n-propanol and 0.01 g of MEHQ were dissolved in 50 ml of THF in a 100 ml two-necked flask with magnetic stirrer and drying tube, and 40 nmol (10.6 g) of bicyclic anhydride (A) were added to this solution. A solution of 40 mmol (4.0 g) of triethylamine and 0.25 g of DMAP in 10 ml of THF was slowly added dropwise accompanied by stirring and cooling with ice (T<10° C.). After the addition was complete, the white suspension became clear and cream-coloured. The reaction was terminated after 30 minutes by adding the reaction mixture to 50 ml of methylene chloride and treating the mixture obtained with 120 ml of 10% aqueous $NaHCO_3$ solution. The organic phase was separated off. The aqueous phase was extracted once more with 50 ml of methylene chloride and adjusted to a pH of 2 with concentrated hydrochloric acid accompanied by cooling. A thick white liquid was precipitated and was taken up in 300 ml of methylene chloride. The aqueous phase was separated off and extracted three times with in each case 150 ml of methylene chloride. The combined organic phases were then stabilized with BHT and dried over $Na_2SO_4$. After the distilling off of the solvent in vacuo at a temperature of below 25° C., a yellow oil was obtained from which a white solid precipitated on standing. After the dissolution of the solid in methylene chloride at room temperature, a white precipitate was deposited by adding petroleum ether. The white precipitate was sucked off, washed with petroleum ether and dried under a medium high vacuum, 3.7 g of (8) (29% yield) being obtained.

Elemental analysis ($C_{16}H_{20}O_7$): Calc.: C, 59.26; H 6.17. Found: C, 58.93; H 6.29.

¹H-NMR (CDCl₃, ppm): 0.95 (m, 3H, CH₃-propyl); 1.7 (m, 2H, CH₂-propyl); 2.0 (s, 3H, CH₃-methacrylic); 3.15 (m, 2H, H-2,3); 4.15 (m, 2H, COOCH₂); 4.75 (m, 2H, CH₂—O-methacrylic); 5.55 (d, 1H, H-4); 5.7 and 6.25 (s, 2H, CH₂=methacrylic); 6.55 (m, 2H, H-5,6); offset (s, 1H, COOH).

IR (KBr, cm⁻¹): 733 (s), 814 (m), 872 (m), 913 (s), 993 (m), 1111 (w), 1167 (s), 1297 (s), 1418 (m), 1455 (m), 1635 (m), 1724 (s), 2969 (m).

The compound (8) served as a model substance in order to facilitate the characterization of the polymerized hybrid monomers according to the invention, e.g. via the molecular masses. This characterization is not easy as formation of network polymers occurs.

Example 8

Radical solution Polymerization of the monomers

Monomer solutions with a monomer concentration of 1.0 mol/l were prepared by dissolving each of the hybrid monomers (2), (3), (4), (5) and (7) according to the invention and the compound (8) acting as a model substance in dimethylformamide (DMF) in a Schlenk vessel. Azobisisobutyronitrile as initiator was added to the respective solution in a quantity such as to give an initiator concentration of 0.02 mol/l. After a Teflon-coated magnetic stirring rod had been inserted, the solutions were degassed in the customary manner, i.e. repeatedly frozen under inert gas and defrosted in vacuo, and then irradiated with UV light at 25° C. in a thermostatically controlled bath accompanied by stirring, using a SUNTEST CPS (Heraeus) rapid radiation table-top unit. The polymerization was terminated after 1 hour by treating the reaction mixture with 10 times the quantity of diethyl ether to precipitate the polymer. The polymer isolated by filtration was then dried under a medium high vacuum until a constant weight was obtained.

The monomer conversion determined for the respective monomer and the number-average molecular weight of the polymer obtained in each case are given in the table below:

| Monomer | Monomer conversion (%) | $M_n$* (g/mol) |
| --- | --- | --- |
| 2 | 43.8 | 9500 |
| 3 | 36.8 | Insoluble, gelling time: 40 minutes |
| 4 | 83.8 | Insoluble, gelling time: 10 minutes |
| 5 | 58.1 | 4960 |
| 7 | 76.1 | Insoluble, gelling time: 15 minutes |
| 8 | 51.2 | 10600 |

$M_n$* - Number-average molecular weight was determined by gel permeation chromatography (GPC) with calibration using polymethyl methacrylate (PMMA) standards

Example 9

Cationic bulk Photopolymerization of (2)

2 g of the hybrid monomer (2) according to the invention together with 1 wt. %, relative to the quantity of monomer, of cationic photoinitiator Degacure Kl 85 (Degussa) were dissolved in a Schlenk vessel in 2 ml of methylene chloride and homogenized. The solvent was then removed under a medium high vacuum, and the sample was degassed in the usual way. The sample was irradiated with UV light for 20 minutes at 25° C. in a thermostatically controlled bath using the SUNTEST CPS (Heraeus) rapid radiation table-top unit.

Unreacted monomer was separated off from the obtained cross-linked polymer by extraction with diethylether. The polymer was then dried under medium high vacuum until a constant weight was obtained. The monomer conversion was 37.5%.

Example 10

Dentine adhesive based on hybrid monomer (5) On the basis of hybrid monomer (5), the preparation of which is described in Example 2, a dentine primer of the following composition was prepared:

Monomer (5): 40.0 wt. %
Water, deionized: 40.0 wt. %
2-hydroxyethyl methacrylate 20.0 wt. %

In order to ascertain the shear strength achieved with this primer formulation as a component of a dentine adhesive, dentine surfaces of extracted, embedded teeth were initially ground flat with 500 and 1000 grade abrasive paper, and the dentine surfaces were dried with compressed air. The formulation was then applied and after 30 seconds the surface was blown off. After that, Syntac adhesive component (Vivadent Ets., Liechtenstein) was applied and distributed with an air blower. Finally, light-curing bonding, namely Heliobond (Vivadent Ets., Liechtenstein) was applied, and it was irradiated. Then the filling composite Tetric (Vivadent Ets., Liechtenstein) was applied in 2 layers and irradiated for 40 seconds in each case. The testpieces obtained were then placed in distilled water and stored there for 25 hours at 37° C. Determination of the shear strength took place according to ISO recommendation ISO-TR 11405: "Dental material—Guidance on testing of adhesion to tooth structure", and resulted in a value of 8±6.4 MPa. An analogous formulation in which the monomer (5) was replaced by further 2-hydroxyethyl methacrylate gave only a value of 2±2.2 MPa.

What is claimed is:

1. Polymerizable hybrid monomers of the following formula (I), and also stereoisomeric compounds and mixtures thereof

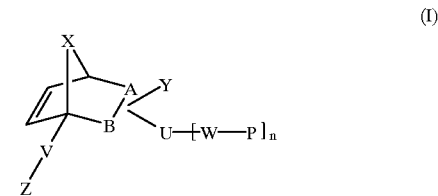

(I)

where A-B, X, Z, V, Y, R, U, R¹, W, P and n independently of one another have the following meanings:

A-B=C—C or C=C;

X=CH₂ or O;

Z=CH₂=CH—CO— or CH₂=C(CH₃)—CO—;

V=CH₂—O or CH₂—NH;

Y=H, substituted or unsubstituted C₁ to C₁₂ alkyl, substituted or unsubstituted C₆ to C₁₄ aryl, halogen, NO₂, NH₂, NR₂, OH, OR, CN, CHO, CO—R, COOH, CO—NH₂, CO—OR, CH₂=CH—, CH₂=CH—CO—, CH₂=C(CH₃)—CO—, SH or S—R, where R=substituted or unsubstituted C₁ to C₁₂ alkyl or substituted or unsubstituted C₆ to C₁₄ aryl;

U=CO—R¹, CO—NHR¹, CO—OR¹, O—CO—NHR¹, NH—CO—OR¹, O—R¹, S—R¹ or is absent, where R¹=C₁ to C₅ alkylene or oxyalkylene or C₆ to C₁₂ arylene;

W=O, NH, CO—O, CO—NH, O—CO—NH or is absent;

P=a polymerizable (meth)acrylic, vinyl, allyl, allyl ether, vinyl ether, epoxy or styryl group; and n=1 to 4.

2. Hybrid monomers according to claim 1, wherein the variables of formula (I) independently of one another have the following meaning:

A-B=C—C or C=C,

X=O,

Z=CH$_2$=C(CH$_3$)—CO—,

V=CH$_2$—O,

Y=COOH, CN or CO—NH$_2$,

R=substituted or unsubstituted C$_1$ to C$_4$ alkyl,

U=CO—OR$^1$ or CO-NHR$^1$,

R=C$_1$ to C$_3$ alkylene,

W=O, NH, CO—O or is absent,

P=a vinyl ether, epoxy, allyl, styryl or (meth)acrylic group, and/or n=1 or 2.

3. Hybrid monomers according to claim 1 comprising at least three groups polymerizable according to difference mechanisms.

4. Process for the preparation of the polymerizable hybrid monomers according to claim 1, wherein a norbornene or norbornadiene compound of the formula (IV) is prepared by way of a Diels-Alder reaction of a substituted diene(meth) acrylic compound of the formula (II) with a substituted dienophile of the formula (III), and, by way of a nucleophilic substitution, (IV) is reacted with the polymerization group-containing educt P-W-H

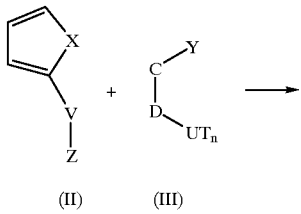

(II)    (III)

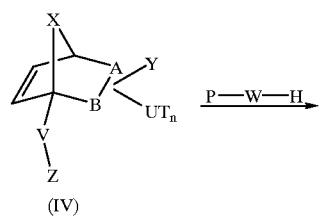

(IV)

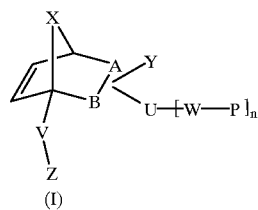

(I)

where

C—D=C=C or C≡C;

H=hydrogen and

T=halogen, OH or OR and the remaining variables are as defined in claim 1.

5. Dental material comprising the polymerizable hybrid monomer according to claim 1.

6. The dental material according to claim 5, wherein the monomer is present in a quantity of from 5.0 to 45 wt. %.

7. The dental material according to claim 5, further comprising one or more compounds selected from the group consisting of polymerizable organic binders, fillers, initiators, and additives.

* * * * *